United States Patent [19]

Temple, Jr.

[11] 4,286,093
[45] Aug. 25, 1981

[54] 9-CYCLOHEXYL-2-ALKOXY-9H-ADENINE PROCESS

[75] Inventor: Davis L. Temple, Jr., Evansville, Ind.

[73] Assignee: Mead Johnson & Company, Evansville, Ind.

[21] Appl. No.: 124,190

[22] Filed: Feb. 25, 1980

[51] Int. Cl.³ .......................................... C07D 473/18
[52] U.S. Cl. ................... 544/276; 424/253; 424/251; 544/254; 544/315
[58] Field of Search ...................... 544/276; 424/253

[56] References Cited

U.S. PATENT DOCUMENTS

| | | | |
|---|---|---|---|
| 3,857,842 | 12/1974 | Asai | 544/276 |
| 3,884,827 | 5/1975 | Asai | 544/276 |
| 4,172,829 | 10/1979 | Naito et al. | 424/253 |

OTHER PUBLICATIONS

Taylor et al., J. Org. Chem. 36(21), 3211, (1971).
Hartman et al., J. Org. Chem. 43(5), 960, (1978).

Primary Examiner—Nicholas S. Rizzo
Attorney, Agent, or Firm—Robert H. Uloth; Robert E. Carnahan

[57] ABSTRACT

A process for preparing 9-cyclohexyl-2-alkoxy-9H-adenine derivatives such as 9-cyclohexyl-2-n-propoxy-9H-adenine from 7-amino-5-(methylthio)[1,2,5]oxadiazolo[3,4-d]pyrimidine and 7-amino-5-(methylthio)[1,2,5]thiadiazolo[3,4-d]pyrimidine is described. Other aspects of the invention are directed to novel intermediates such as the compound 4-amino-6-(cyclohexylamino)-5-(formylamino)-2-(methylthio)pyrimidine.

3 Claims, No Drawings

9-CYCLOHEXYL-2-ALKOXY-9H-ADENINE PROCESS

BACKGROUND OF THE INVENTION

This invention describes a new, improved process for synthesis of 9-cyclohexyl-2-alkoxy-9H-adenine derivatives and in particular to preparation of the non-adrenergic bronchodilating agent 9-cyclohexyl-2-n-propoxy-9H-adenine.

Regarding previous synthesis of such compounds, Naito, et al., U.S. Pat. No. 4,172,829 disclose methods for converting 2,6-dichloropurine (1) to 9-cyclohexyl-2-alkoxy-9H-adenine (7) as depicted in the reaction scheme below wherein R is $C_1$–$C_6$ alkyl, M is Na, K, Tl, Ag, or HgCl, X is Cl, Br or I, and Alk is sodium or potassium.

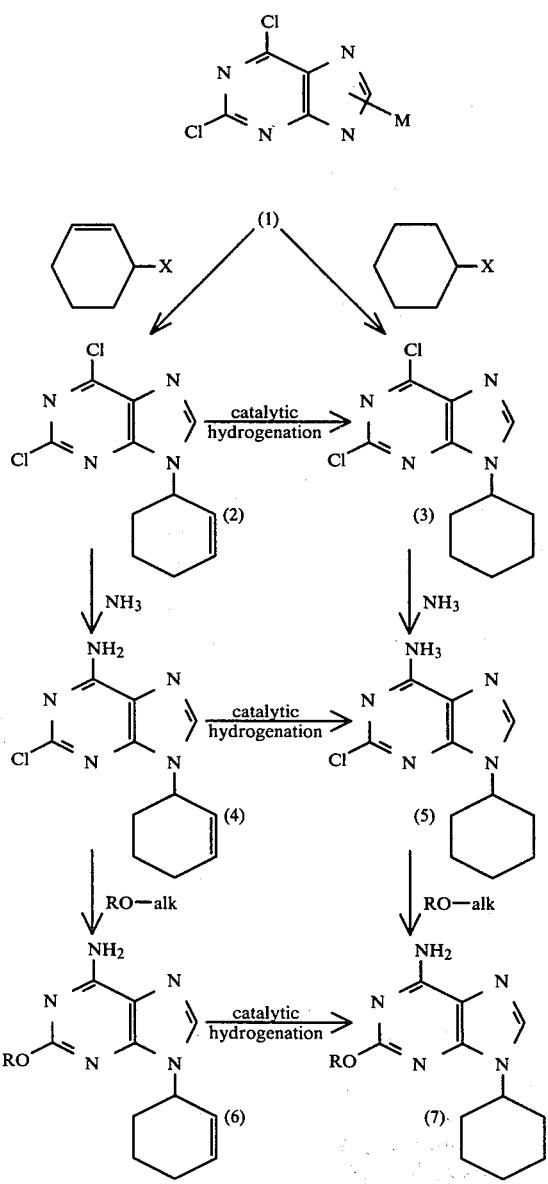

E. C. Taylor, et al., J. Org. Chem., 36(21), 3211 (1971) describe preparation of 2-, 8-, and 9-substituted adenines (6) according to the following outline.

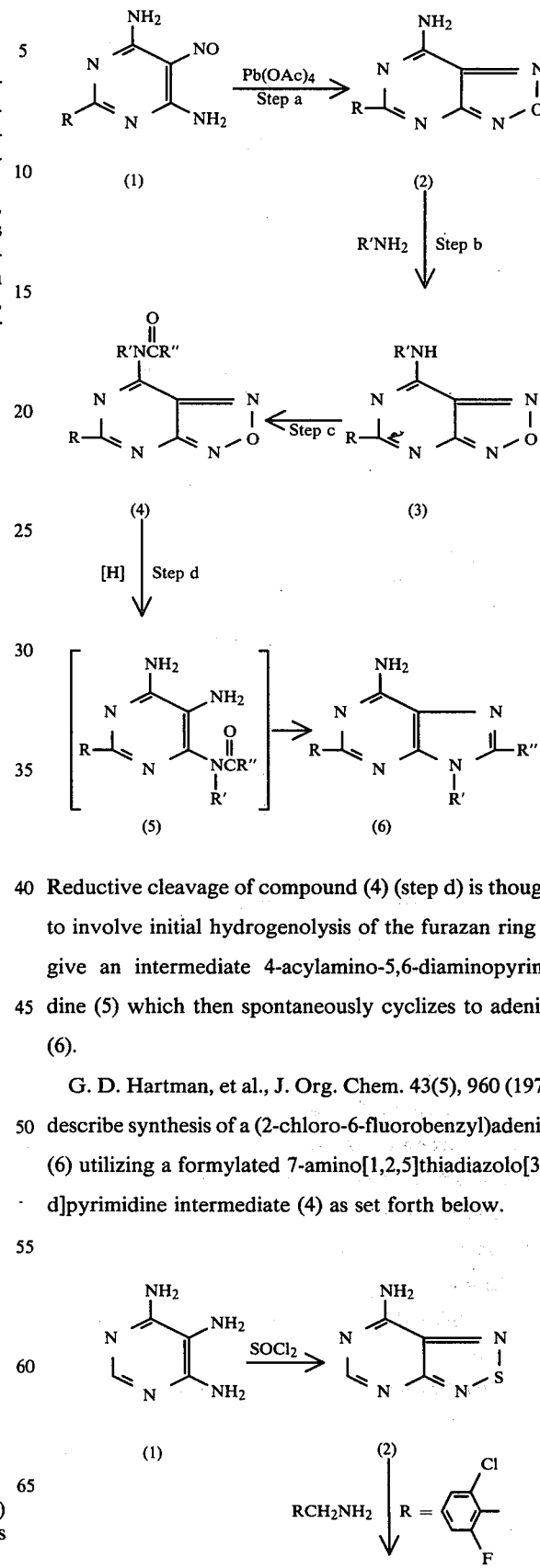

Reductive cleavage of compound (4) (step d) is thought to involve initial hydrogenolysis of the furazan ring to give an intermediate 4-acylamino-5,6-diaminopyrimidine (5) which then spontaneously cyclizes to adenine (6).

G. D. Hartman, et al., J. Org. Chem. 43(5), 960 (1978) describe synthesis of a (2-chloro-6-fluorobenzyl)adenine (6) utilizing a formylated 7-amino[1,2,5]thiadiazolo[3,4-d]pyrimidine intermediate (4) as set forth below.

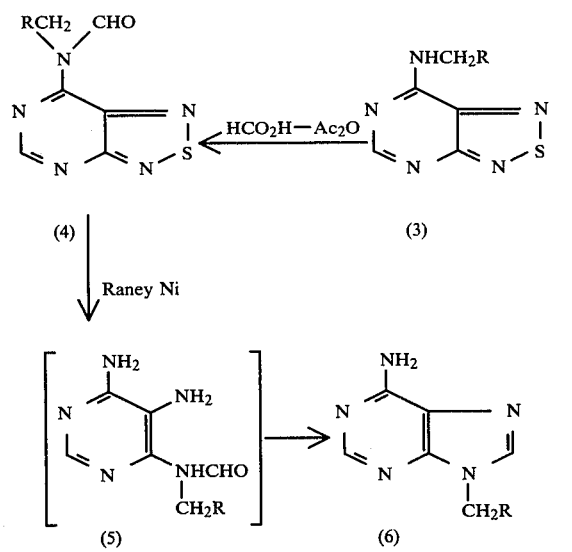

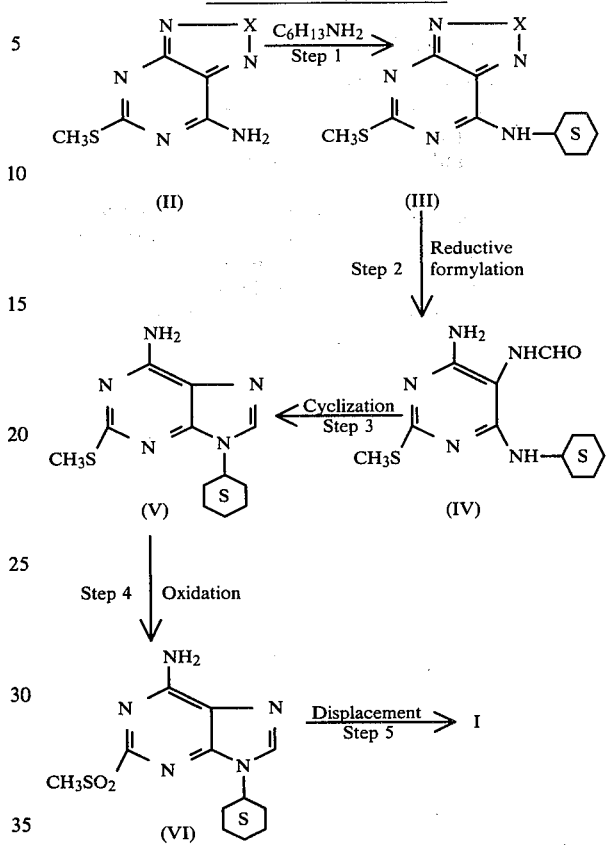

DETAILED DESCRIPTION OF THE INVENTION

Adenine derivatives prepared according to the invention are characterized by structural Formula I numbered according to the chemical nomenclature system employed herein.

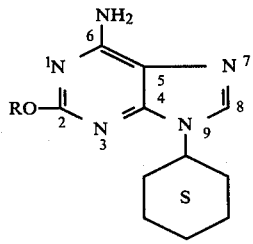

For the purpose of this disclosure, the R substituent represents an alkyl group of 1 to 6 carbon atoms inclusive including those having either straight or branched hydrocarbon chains. Particularly preferred alkyl groups are those having from 1 to 4 carbon atoms with the most preferred being n-propyl. Other examples of suitable $C_1$-$C_6$ alkyl groups include methyl, ethyl, isopropyl, n-butyl, isobutyl, t-butyl, n-pentyl, n-hexyl, and the like.

The following flow chart illustrates the process of the present invention for converting 7-amino-5-(methylthio)[1,2,5]oxadiazolo[3,4-d]pyrimidine (IIa, X=O) and 7-amino-5-(methylthio)[1,2,5]thiadiazolo[3,4-d]pyrimidine (IIb, X=S) to 2-alkoxy-9-cyclohexyladenines of Formula I.

Diazolo starting materials of Formula II required for the instant process are prepared as described by E. C. Taylor, et al., supra. (IIa, X=O) or according to the general method of G. D. Hartman, et al., supra, (IIb, X=S).

Step 1 of the process outlined above is carried out by reacting the diazolo[3,4-d]pyrimidine intermediate (II, X=O, S) with from 1 to 2 mole equivalents of cyclohexylamine in an aprotic inert solvent (i.e. a solvent non-reactive with components of the reaction mixture under the reaction conditions maintained) such as acetonitrile or N,N-dimethylformamide. The reaction is preferably conducted at temperatures ranging from about 20° to about 130°. With the solvent acetonitrile, the reaction is preferably carried out at reflux temperature whereas, with N,N-dimethylformamide, room temperature is preferred.

In Step 2, reductive formylation of the diazolo[3,4-d]pyrmidine intermediate III affords the formylaminopyrimidine intermediate IV in yields ranging from 88 to 98%. In the case of the oxadiazolo intermediate (III, X=O) formylation is preferably carried out by catalytic hydrogenation employing 10% palladium-on-carbon with formic acid as the solvent. In the case of the thiadiazolo intermediate (III, X=S), formylation is preferably carried out with Raney nickel employing formic acid as solvent.

In Step 3, cyclization of the formylaminopyrimidine IV is readily effected by heating the with an alkali metal base such as sodium hydroxide or potassium hydroxide in aqueous solution or a mixture of ethanol-water.

In Step 4, oxidation of the methylthio intermediate V to the corresponding methyl sulfone VI is carried out with the suitable oxidizing agent such as meta-chloroperbenzoic acid and the like. Conversion of V to the sulfone VI takes place via the methylsulfoxide intermediate, 6-amino-9-cyclohexyl-2-(methylsulfinyl)purine which also provides similar yields of Formula I adenine products when reacted with RO-alk according to Step 5.

The final Step (5) of the process wherein the methylsulfonyl radical is displaced, is accomplished by heating the methylsulfone intermediate VI with an alkoxide of the formula RO-alk in alkanol solvent (i.e., ROH) wherein alk is sodium or potassium and R is as defined above.

As depicted above, the process of the present invention for preparing an adenine derivative of Formula I comprises consecutive steps of:

(1) reacting a diazolo[3,4-d]pyrimidine of Formula II wherein X is oxygen or sulfur

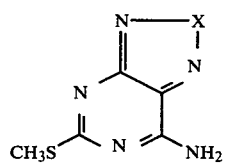

with 1 to 2 equivalents of cyclohexylamine in an inert reaction solvent at a temperature ranging from 20°–130° to produce the diazolo[3,4-d]pyrimidine of Formula III wherein X is oxygen or sulfur;

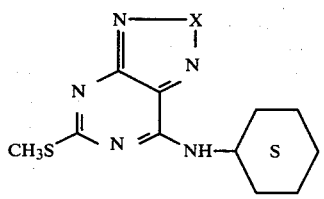

(2) reductively formylating III in 50–100% formic acid employing, when X is oxygen, catalytic hydrogenation with palladium-on-carbon catalyst or when X is sulfur, Raney nickel, to produce the formylated compound of Formula IV;

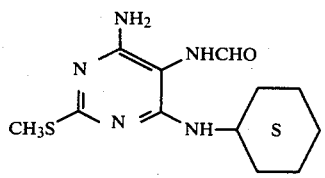

(3) cyclizing IV with alkali metal hydroxide to produce the adenine derivative of Formula V;

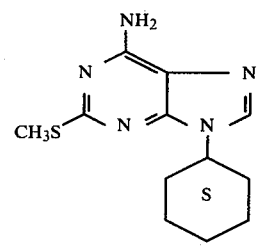

(4) oxidizing V in an inert solvant to produce sulfone VI;

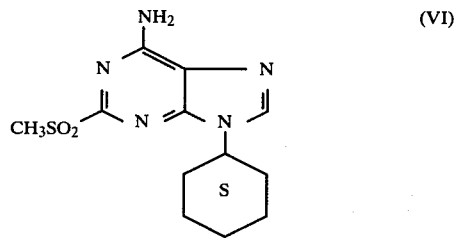

(5) displacing the methylsulfone radical of VI with an alkali metal alkoxide of the formula RO-alk wherein alk represents sodium or potassium and R is 1 to 6 carbon atoms inclusive in an inert reaction solvant to produce a 2-alkoxy-9-cyclohexyladenine of Formula I.

Representative examples of Formula I adenines provided by the above process employing appropriate RO-alk reactants in Step 5 are:

Ia. 9-cyclohexyl-2-n-propoxy-9H-adenine,

Ib. 9-cyclohexyl-2-ethoxy-9H-adenine, and

Ic. 9-cyclohexyl-2-n-butoxy-9H-adenine.

A preferred embodiment of the invention is directed to a process for preparing 6-amino-9-cyclohexyl-2-(n-propoxy)purine comprising consecutive steps of reductively formylating 2-(cyclohexylamino)-5-(methylthio)[1,2,5]oxadiazolo[3,4-d]pyrimidine in formic acid with palladium-on-carbon catalyst to produce 4-amino-6-(cyclohexylamino)-5-(formylamino)-2-(methylthio)pyrimidine;

cyclizing 4-amino-6-(cyclohexylamino)-5-(formylamino)-2-(methylthio)pyrimidine with an alkali metal base in aqueous or alkanol solvent to produce 6-amino-9-cyclohexyl-2-(methylthio)purine;

oxidizing 6-amino-9-cyclohexyl-2-(methylthio)purine with m-chloroperbenzoic acid in an inert solvent (e.g. acetic acid) to produce 6-amino-9-cyclohexyl-2-(methylsulfonyl)purine; and reacting 6-amino-9-cyclohexyl-2-(methylsulfonyl)purine with sodiumn-propoxide or potassium n-propoxide in n-propanol to displace the methylsulfonyl radical and produce 6-amino-9-cyclohexyl-2-(n-propoxy)purine.

The following examples further illustrate the present invention and will enable those skilled in the art to understand it more completely. All temperatures expressed herein are in degrees centigrade.

EXAMPLE 1

7-Amino-5-(methylthio)[1,2,5]oxadiazolo[3,4-d]pyrimidine (IIa)

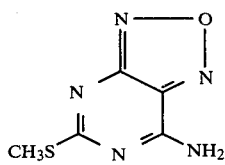

Methyl iodide (169.0 g., 1.19 mole) is added in one portion to a stirred solution of 4,6-diaminopyrimidine-2(1H)thione (146 g., 1.02 mole) in 1.0 liter 1N sodium hydroxide. The thione starting material is obtained by reaction of thiourea and malononitrile according to Kikugawa, et al., Chem. Pharm. Bull., 25(7), 1811-1821 (1977). In about five minutes following the addition a precipitate forms. After stirring overnight, the reaction mixture is filtered and air-dried affording 135.1 g. (81%) of 4,6-diamino-2-(methylthio)pyrmidine; m.p. 185°–186° (recrystallized from acetonitrile).

Sodium nitrite (48.3 g., 0.7 mole) added in one portion to a stirred suspension of 4,6-diamino-2-(methylthio)-pyrimidine (95.0 g., 0.6 mole) in a mixture of 950 ml. water and 285 ml. acetic acid forms a thick, blue slurry which is stirred for a 6 hr. period. The product is collected on a filter and oven dried overnight to afford 108.6 g. (97%) of 4,6-diamino-2-(methylthio-5-nitrosopyrimidine as a blue solid, m.p. 254°–255°.

Lead tetraacetate (221.0 g., 0.5 mole) is added in one portion to a stirred suspension of 4,6-diamino-2-(methylthio)-5-nitrosopyrimidine (89.0 g., 0.48 mole) in 2.4 liter acetic acid. The reaction mixture is stirred for 1.5 days and the yellow solid which forms collected by filtration with a second crop isolated by partial concentration of the filtrate to provide a total yield of 64.3 g. (73%) of 7-amino-5-(methylthio)[1,2,5]-oxadiazolo[3,4-d]pyrimidine, m.p. 240°–243°. Crystallization from dimethylformamide-water followed by a second crystallization from acetonitrile-water affords yellow crystals of this material with melting point unchanged.

Anal. Calcd. for $C_5H_5N_5OS$: C, 32.78; H, 2.75; N, 38.23. Found: C, 32.57; H, 2.73; N, 38.06.

EXAMPLE 2

7-(Cyclohexylamino)-5-(methylthio)[1,2,5]-oxadiazolo[3,4-d]pyrimidine (IIIa)

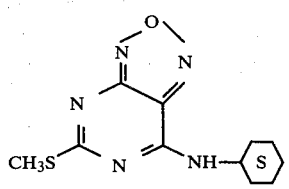

A mixture of 7-amino-5-(methylthio)[1,2,5]oxadiazolo[3,4-d]pyrmidine (52.3 g., 0.29 mole) and cyclohexylamine (56.5 g., 0.58 mole) in 175 ml. dry acetonitrile is heated at reflux with stirring for a 2 hr. period during which time ammonia evolution occurs and a solution slowly forms. After cooling and filtering the solution, the filtrate is diluted with acetonitrile to produce a yellow-green precipitate which is collected on a filter and air-dried to yield 64.0 g. (86%) of 7-(cyclohexylamino)-5-(methylthio)[1,2,5]oxadiazolo[3,4-d]pyrimidine, m.p. 129°–130°. Crystallization from acetonitrile-water affords analytically pure material of unchanged melting point.

Anal. Cacld. for $C_{11}H_{15}N_5OS$: C, 49.80; H, 5.70; N, 26.40. Found: C, 49.80; H, 5.65; N, 26.21.

EXAMPLE 3

4,5,6-Triamino-2-(methylthio)pyrimidine

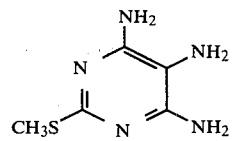

Sodium hydrosulfite (sodium dithionite, 78.3 g., 0.45 mole) is added in one portion to a stirred suspension of 4,6-diamino-2-(methylthio)-5-nitrosopyrimidine (27.8 g., 0.15 mole) in 300 ml. 1 N sodium hydroxide. Within a 15-20 minute period, the temperature of the mixture increases to 60° with concomitant foaming. The mixture is stirred for a 16 hr. period, insolubles collected and washed well with water, air-dried, and crystallized from acetonitrile to yield 19.73 g. (76.8%) of 4,5,6-triamino-2-(methylthio)pyrimidine as yellow crystals, m.p. 180°–182°.

EXAMPLE 4

7-Amino-5-(methylthio)[1,2,5]thiadiazolo[3,4-d]pyrimidine (IIb)

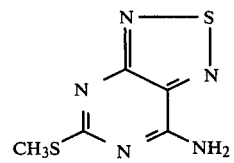

A mixture of 4,5,6-triamino-2-(methylthio)pyrimidine (5.14 g., 0.03 mole) and thionyl chloride (32.12 g., 0.27 mole) is refluxed with stirring for an 18 hr. period. Excess thionyl chloride is removed under reduced pressure, 40 ml. of water added to the residue and the suspension mixture adjusted to pH 8 with saturated sodium bicarbonate solution. Insolubles are collected, washed with water and air-dried to provide 4.7 g. (78.3%) of 7-amino-5-(methylthio)[1,2,5]thiadiazolo[3,4-d]pyrimidine, m.p. 197°–199°.

Anal. Calcd. for $C_5H_5N_5S_2$: C, 30.15; H, 2.53; N, 35.15. Found: C, 29.82; H, 2.40; N, 35.01.

EXAMPLE 5

7-(Cyclohexylamino)-5-(methylthio)[1,2,5]-thiadiazolo[3,4-d]pyrimidine (IIIb)

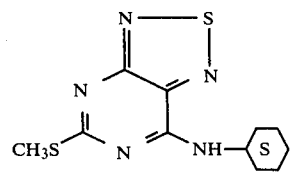

A mixture of 7-amino-5-(methylthio)[1,2,5]-thiadiazolo[3,4-d]pyrimidine (16.9 g., 0.085 mole) and cyclohexylamine (34.0 g., 0.34 mole) is stirred and heated at 105°-110° for a 20 hr. period. To the cooled reaction mixture is added 50 ml. of water and 50 ml. of hexane. Insolubles are collected and crystallized from hexane to give a material having two spots on TLC (silica gel, CHCl$_3$-EtOH, 9:1). The material is purified by column chromatography employing 180 g. silica gel using chloroform as the eluent. All fractions showing a single component on TLC (higher R$_f$ spot) are combined and concentrated in vacuo affording a solid which triturated with hexane yields 9.75 g. (41%) of 7-(cyclohexylamino)-5-(methylthio)[1,2,5]-thiadiazolo[3,4-d]pyrimidine, m.p. 134°-136°.

Anal. Calcd. for C$_{11}$H$_{15}$N$_5$S$_2$: C, 46.96; H, 5.38; N, 24.89 Found: C, 46.98; H, 5.46; N, 24.90.

EXAMPLE 6

4-Amino-6-(cyclohexylamino)-5-(formylamino)-2-(methylthio)pyrimidine (IV)

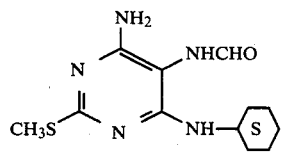

Method A.

2-(Cyclohexylamino)-5-(methylthio)[1,2,5]oxadiazolo[3,4-d]pyrimidine (54.0 g., 0.20 mole) is hydrogenated in 350 ml. 90% formic acid employing 5.0 g. of 10% palladium-on-carbon as catalyst. After the reduction is complete (about 2.5 hr.), the catalyst is collected on a filter employing diatomaceous earth and the filtrate concentrated in vacuo to yield a viscous oil. Water is added to the residual oil and the mixture made basic with concentrated ammonia or a solution of 50% sodium hydroxide. The resulting white solid is filtered and air-dried yielding 50.2 g. (88%) of 4-amino-6-(cyclohexylamino)-5-(formylamino)-2-(methylthio)pyrimidine. Crystallization from chloroform-hexane affords analytically pure material as white crystals, m.p. 200°-201°.

Anal. Calcd. for C$_{12}$H$_{19}$N$_5$OS.¼H$_2$O: C, 50.42; H, 6.87; N, 24.68. Found: C, 50.61; H, 6.80; N, 24.68.

NMR: 8.09 ppm, s, 1H and 8.60, s, 1H; NH-CHO; 5.86, m, 3H; NH, NH$_6$.

Method B.

Formic acid (90%, 100 ml.) is added to a mixture of 7-(cyclohexylamino)-5-(methylthio)[1,2,5]-thiadiazolo[3,4-d]pyrimidine (3.82 g., 0.014 mole) and 15.28 g. Raney nickel. When the reaction is complete as shown by disappearance of starting material according to TLC (CHCl$_3$-EtOH, 9:1), diatomaceous earth is added and the mixture filtered. Concentration of the filtrate in vacuo provides a residue which is stirred with 50 ml. of ethanol and filtered. Concentration of the filtrate in vacuo affords 4.46 g. (98%) of 4-amino-6-(cyclohexylamino)-5-(formylamino)-2-(methylthio)pyrimidine formate salt as a thick oil which can be used in Example 7 without further purification.

EXAMPLE 7

6-Amino-9-cyclohexyl-2-(methylthio)purine (V)

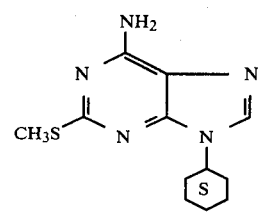

A solution of 4-amino-6-(cyclohexylamino)-5-(formylamino)-2-(methylthio)pyrimidine (25.0 g., 0.088 mole) or a mole equivalent of the formate salt thereof in 125 ml. ethanol and 500 ml. 1 N sodium hydroxide is refluxed for a 4 hr. period, cooled in an ice-bath, and then filtered affording 14.1 g. (61%) of yellow material. Crystallization from ethanol gives 6-amino-9-cyclohexyl-2-(methylthio)purine as off-white crystals, m.p. 222°-224°.

Anal. Calcd. for C$_{12}$H$_{17}$N$_5$S: C, 54.73; H, 6.51; N, 26.59. Found: C, 54.62; H, 6.72; N, 26.63.

EXAMPLE 8

6-Amino-9-cyclohexyl-2-(methylsulfonyl)purine (VI)

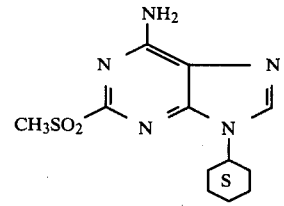

A solution of approximately 80% pure m-chloroperbenzoic acid (430 g., 2.0 mole) in 540 ml. of ethanol is added dropwise over a 1 hr. period to a solution of 6-amino-9-cyclohexyl-2-(methylthio)purine (250 g., 0.95 mole) in 1.2 liter of acetic acid while maintaining a reaction temperature of 35°-40°. Following the addition, the reaction mixture is stirred for 0.5 hr., mixed with 6 liter of water with rapid stirring and then filtered. The filter-cake is first washed with water and then suspended in 5 liter of water. Concentrated potassium hydroxide is added to this suspension with vigorous stirring until the mixture is strongly basic. Suspended material is then collected, washed with water and air-dried to provide 248 g. (88.6%) of 6-amino-9-cyclohexyl-2-(methylsulfonyl)purine, m.p. 272°-274°.

EXAMPLE 9

6-Amino-9-cyclohexyl-2-(n-propoxy)purine (Ia)

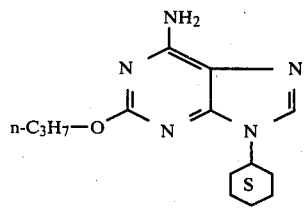

6-Amino-9-cyclohexyl-2-(methylsulfonyl)purine (61 g., 0.207 mole) is added in one portion to 0.414 mole of sodium n-propoxide in 800 ml. of n-propanol. The mixture is refluxed for a 6 hr. period and then concentrated under reduced pressure. Stirring the residual oily material with water provides a solid which is collected and crystallized from acetonitrile-water yielding 53 g. (93%) of 6-amino-9-cyclohexyl-2-(n-propoxy)purine, m.p. 146°–148°.

What is claimed is:

1. A process for preparing 9-cyclohexyl-2-alkoxy-9H-adenine derivatives of Formula I

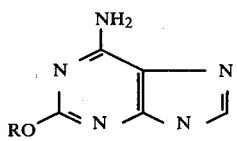

which comprises the consecutive steps of:

(1) reacting a diazolo[3,4-d]pyrimidine of Formula II wherein X is oxygen or sulfur

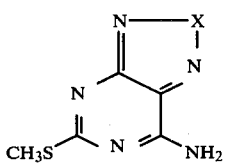

with 1 to 2 equivalents of cyclohexylamine in an inert reaction solvent at a temperature ranging from 20°–130° to produce the diazolo[3,4-d]pyrimidine of Formula III wherein X is oxygen or sulfur;

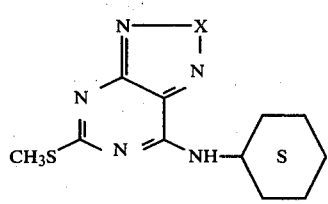

(2) reductively formylating III in 50–100% formic acid employing, when X is oxygen, catalytic hydrogenation with palladium-on-carbon catalyst or when X is sulfur, Raney nickel, to produce the formylated compound of Formula IV;

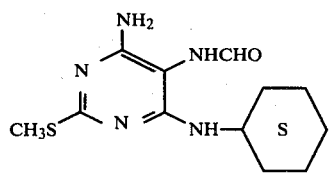

(3) cyclizing IV with alkali metal hydroxide to produce the adenine derivative of Formula V;

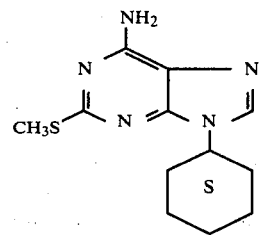

(4) oxidizing V in an inert solvant to produce sulfone VI;

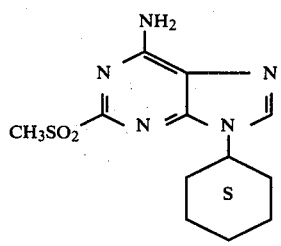

(5) displacing the methylsulfone radical of VI with an alkali metal alkoxide of the formula RO-alk wherein alk represents sodium or potassium and R is 1 to 6 carbon atoms inclusive in an inert reaction solvent to produce a 2-alkoxy-9-cyclohexyladenine of Formula I.

2. The process of claim 1 wherein in Step 1 the Formula II compound 7-amino-5-(methylthio)[1,2,5]oxadiazolo[3,4-d]pyrimidine is employed and in Step 5 the alkoxide is sodium n-propoxide to produce 6-amino-9-cyclohexyl-2-(n-propoxy)purine.

3. A process for preparing 6-amino-9-cyclohexyl-2-(n-propoxy)purine which comprises the consecutive steps of:

reductively formylating diazolo[3,4-d]pyrimidine of Formula IIIa

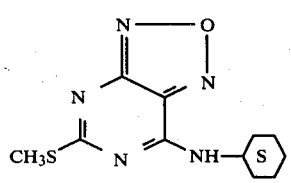

in 85–98% formic acid with palladium-on-carbon catalyst to produce the formylated compound of Formula IV;

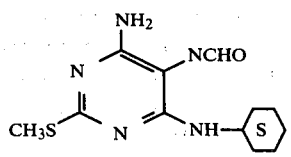

cyclizing IV by heating with aqueous sodium hydroxide solution to produce the adenine derivative of Formula V;

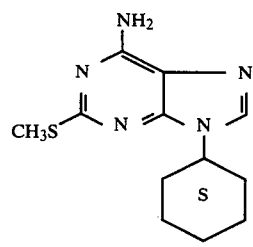 (V)
oxidizing V with meta-chloroperbenzoic acid in acetic acid to produce the sulfone of Formula VI;
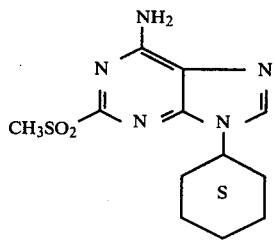 (VI)
displacing the methylsulfone radical of VI with sodium n-propoxide in n-propanol to produce 6-amino-9-cyclohexyl-2-(n-propoxy)purine.
* * * * *